United States Patent
Ishikawa et al.

(10) Patent No.: US 6,264,611 B1
(45) Date of Patent: Jul. 24, 2001

(54) MONITOR FOR INTERVENTIONAL PROCEDURES

(75) Inventors: Akira Ishikawa, Royce City; Nabuo Takeda, Richardson; Suzanne I. Ahn, Dallas, all of TX (US); Samuel S. Ahn, Los Angeles, CA (US); Steven R. Hays, Dallas, TX (US); F. Andrew Gaffney, Nashville, TN (US)

(73) Assignee: Ball Semiconductor, Inc., Allen, TX (US)

( * ) Notice: Subject to any disclaimer, the term of this patent is extended or adjusted under 35 U.S.C. 154(b) by 0 days.

(21) Appl. No.: 09/448,644

(22) Filed: Nov. 24, 1999

Related U.S. Application Data

(60) Provisional application No. 60/110,040, filed on Nov. 25, 1998.

(51) Int. Cl.$^7$ .................................................. A61B 5/02
(52) U.S. Cl. ........................... 600/486; 600/485; 600/488
(58) Field of Search ............................... 600/486, 488, 600/485, 483, 481, 585

(56) References Cited

U.S. PATENT DOCUMENTS

| | | | |
|---|---|---|---|
| 4,554,929 | * 11/1985 | Samson et al. | 600/585 |
| 4,722,348 | * 2/1988 | Ligtenberg et al. | 600/488 |
| 4,884,579 | * 12/1989 | Engelson | 600/585 |
| 4,886,067 | * 12/1989 | Palermo | 600/434 |
| 5,292,315 | * 3/1994 | Eutenuer | 600/528 |
| 5,365,942 | * 11/1994 | Shank | 600/585 |
| 5,373,852 | 12/1994 | Harrison et al. . | |
| 5,465,733 | * 11/1995 | Hinohara et al. | 600/585 |
| 5,715,827 | * 2/1998 | Corl et al. | 600/486 |
| 5,720,300 | * 2/1998 | Fagan et al. | 600/585 |
| 5,807,265 | * 9/1998 | Itoigawa et al. | 600/486 |
| 5,836,886 | * 11/1998 | Itoigawa et al. | 600/488 |
| 5,955,776 | * 9/1999 | Ishikawa | 257/618 |
| 6,019,728 | * 2/2000 | Itoigawa et al. | 600/486 |
| 6,019,729 | * 2/2000 | Itoigawa et al. | 600/488 |
| 6,106,476 | * 8/2000 | Corl et al. | 600/486 |
| 6,120,457 | * 9/2000 | Coombes et al. | 600/486 |

FOREIGN PATENT DOCUMENTS

| | | | |
|---|---|---|---|
| WO 94/22367 | 10/1994 | (WO) | A61B/5/05 |
| WO 98/29030 | 7/1998 | (WO) | A61B/5/02 |

* cited by examiner

*Primary Examiner*—John P. Lacyk
*Assistant Examiner*—Navin Natnithithadha
(74) *Attorney, Agent, or Firm*—Howison, Chauza, Thoma, Handley & Arnott, L.L.P.

(57) ABSTRACT

A ball-shaped semiconductor monitoring device (150) having one or more transducer functions for use with an instrument that is insertable into a human body. In one disclosed embodiment, a needle (130) and modified stylet (140) are inserted into intraluminal body cavities for measuring fluid pressure. The modified stylet (140) has the monitoring device (150) attached to one end. The stylet (140) has a metal annulus (142) extending throughout its length and a communication wire (144) disposed therein. The wire (144) is surrounded by an insulator (146) to electrically isolate it from the stylet (140). A recessed cavity (148) is provided at the distal end of the stylet (140) to accommodate the ball monitoring device (150). A transducer (152) is integrated on the ball device (150) to measure such quantitative conditions as pressure. The ball (150) has a ground terminal (154) and a data terminal (156). The ground terminal (154) is electrically connected to the metal annulus (142) of the stylet (140) by a solder joint (158). The data terminal (156) is connected to the communication wire (144) by a contact (160). The instrument that carries the semiconductor device to a particular site within the body may be a catheter, guidewire, stylet, needle or any other insertable instrument. The transducer can be fabricated to sense pressure, fluid flow rate, temperature and other physiological parameters and physical conditions.

40 Claims, 10 Drawing Sheets

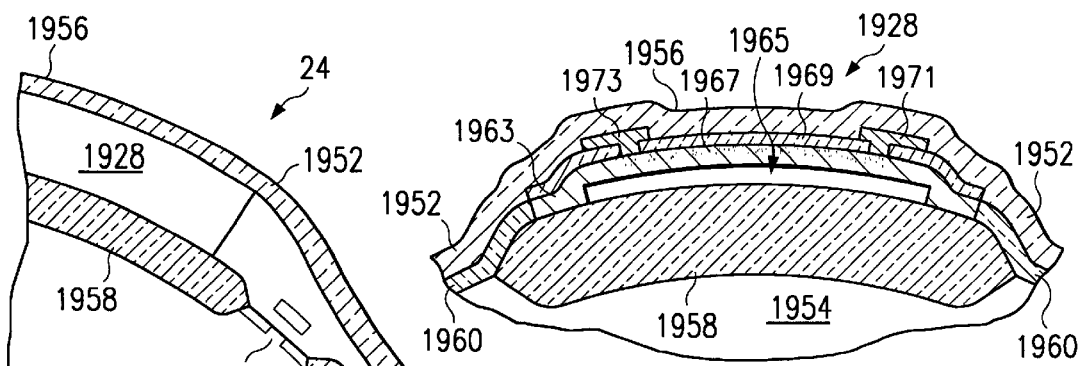
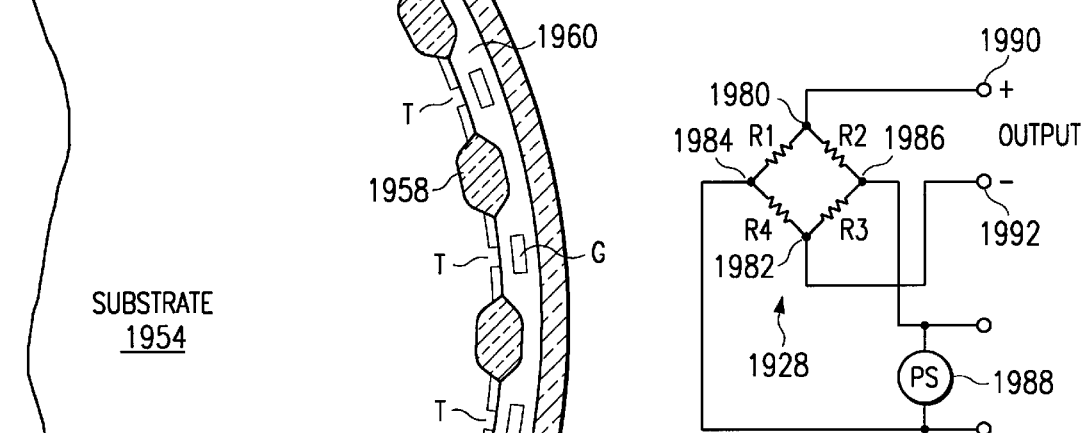
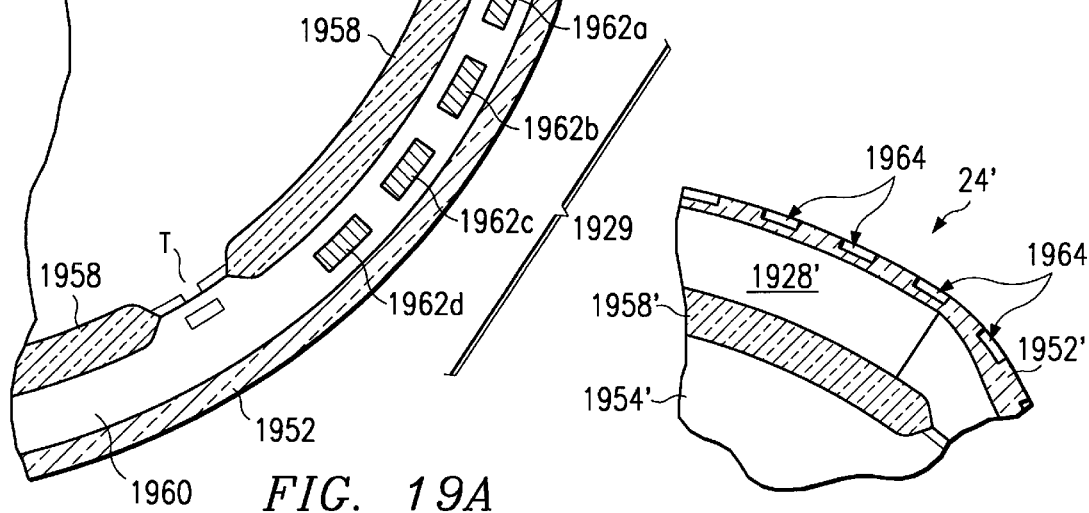

MONITOR FOR INTERVENTIONAL PROCEDURES

CROSS-REFERENCE TO RELATED APPLICATIONS

This application claims priority under 35 U.S.C. 119(e) from U.S. Provisional Patent Application Ser. No. 60/110,040 filed on Nov. 25, 1998, having the same title as this application.

This application is related to co-pending U.S. patent application Ser. No. 09/323,585 entitled "IMPLANTABLE EPICARDIAL ELECTRODE," filed on Jun. 1, 1999; U.S. patent application Ser. No. 09/586,200, entitled "GLUCOSE SENSOR," filed on Jun. 2, 2000; U.S. patent application Ser. No. 09/448,781, entitled "SPHERICALLY-SHAPED BIOMEDICAL IC," filed Nov. 24, 1999 ; U.S. patent application Ser. No. 09/448,642 entitled "MINIATURE SPHERICAL-SHAPED SEMICONDUCTOR WITH TRANSDUCER," filed Nov. 24, 1999; and U.S. patent application Ser. No. 09/448,638 entitled "INTERNAL THERMOMETER," filed Nov. 24, 1999.

TECHNICAL FIELD OF THE INVENTION

This invention is related to physiological monitoring devices and systems, and more particularly to miniature sensors and diagnostic equipment for minimally invasive medical procedures.

BACKGROUND OF THE INVENTION

Catheters, guidewires, stylets, and needles are used in most areas of medicine, particularly in cardiology, radiology, and surgery, to monitor various physical, physiologic and hemodynamic parameters such as pressure, flow, velocity, vessel caliber, pH, $pO_2$, $pCO_2$, and temperature. Catheters and guidewires can also function as tools to perform diagnostic imaging (angiograms) and to deliver treatment (angioplasty, physical and electrical ablation of lesions). Existing technology requires these catheters and guidewires to be directly connected by a fluid column or wired to external sensing equipment to measure most of these various physiologic parameters.

Catheters and guidewires can be used for diagnostic and treatment modalities within the urogenital system, which includes the bladder, ureters, urethra and the kidneys. When obstructive processes involve these areas, they can endanger kidney function. Similarly, pancreatic-biliary ductal systems can become obstructed by stones, strictures or tumors. In the gastrointestinal tract, the catheters and guidewires can be passed orally or transrectally and measure such parameters as pH, temperature, or hemoglobin. Monitors placed in the cervical canal can be used to assess uterine contractions, intrauterine pressure, fetal heart rate, $pO_2$ and pH. Pressure monitors can also be placed at the end of small catheters or guidewires located in the tracheobronchial tree to monitor peak end-expiratory airway pressures of patients requiring mechanical ventilation. Current technology only allows for indirect measurement of this value at the level of the ventilator itself. A catheter tipped with a pressure sensor for directly monitoring peak end-expiratory pressures is desired for allowing physicians to better modulate ventilatory therapy.

Existing clinical cardiorespiratory technology uses fluid-filled central venous and balloon tipped pulmonary artery catheters to measure pulmonary artery pressure, central venous pressure, pulmonary capillary wedge pressure, temperature, and oxygen saturation. Cardiac output and systemic vascular resistance can then be derived. These pulmonary artery catheters are referred to as Swan-Ganz Catheters (or balloon-tipped, flow-directed catheters). Limitations of these catheters are described in detail above. Typically, pressure, temperature and pulmonary artery hemoglobin oxygen saturation are monitored directly while $pO_2$, pH, $pCO_2$ are measured in the laboratory from a blood sample drawn from the catheter.

Current technology also has limitations imposed by the properties of fluid within the catheter; the distance to the external transducer; properties of the material used in catheter construction, and size constraints which can lead to distortion and damping of the signal and creation of artifacts limiting precision and response frequency. Medical engineering's ability to diminish catheter size is currently limited by either wiring and/or open fluid column requirements. In some instances, patient mobility and transport are currently restricted by requirement for connection to an external monitor. Precise alignment of the catheter tip and the external sensing equipment is required with open fluid column-containing catheters to eliminate gravitational effects on hydrostatic pressure. The pH, $pCO_2$, and $pO_2$ of body fluids are usually determined by removal of blood from the external opening of the catheter; a slow, cumbersome process with risk for catheter occlusion via blood clotting and for blood-borne pathogen exposure. The removal of blood, and the requirement to discard a portion of the blood, often leads to an anemia in patients undergoing extensive monitoring or interventional procedures.

A common diagnostic and therapeutic procedure for vascular disease is an angiogram followed by an angioplasty. An angiogram is obtained with fluoroscopic imaging when radio-opaque contrast is injected into the artery through the open, hollow catheter. Once the target lesion is identified, the diagnostic catheter is exchanged over a guidewire for the balloon angioplasty catheter. The guidewire is then passed across the stenotic lesion. Once the wire crosses the lesion, a balloon angioplasty catheter is passed coaxially over the wire and placed at the site of the stenosis. The lesion is then dilated by inflating the balloon to open the channel. The pressure measurement through this open hollow catheter is virtually impossible with the wire in place. However, removal of the wire will cause loss of position across the "treated" lesion where a pressure gradient may still exist, requiring further angioplasty. Repeated insertion of guidewires and balloon-tipped catheters across vascular lesions may create atheroemboli, endothelial damage, thrombosis of the vessel, and dissection of the arterial wall.

SUMMARY OF THE INVENTION

The present invention disclosed and claimed herein, in one aspect thereof, comprises a monitoring system having an instrument that is insertable in a living body, the instrument having a distal end for accessing a site within the body and a proximal end that remains outside the body. A miniature semiconductor device is affixed at a point on the distal end of the instrument, the semiconductor device including a transducer for converting information from one medium to another. An external monitoring station is in communication with the semiconductor device, and information can be transferred between the semiconductor device and the monitoring station.

BRIEF DESCRIPTION OF THE DRAWINGS

For a more complete understanding of the present invention and the advantages thereof, reference is now made to the following description taken in conjunction with the accompanying Drawings in which:

FIGS. 19A–19D illustrate a circuit diagram for a transducer, an equivalent device structure for the transducer, and other device structures, according to a disclosed embodiment.

DETAILED DESCRIPTION OF THE INVENTION

Figure 1:
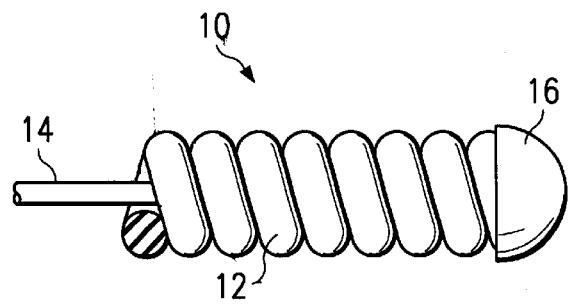
FIG. 1 illustrates a schematic partial side view of the distal end of a prior art guidewire of the type typically used with catheters in balloon angioplasty procedures.

The disclosed architecture addresses the problems and equipment limitations in the prior art by exploiting advances in the miniaturization of electronic devices. A significant departure from conventional semiconductor device manufacturing processes is described in, commonly-assigned U.S. Pat. No. 5,955,776, filed May 16, 1997, issued Sep. 21, 1999 and entitled "Spherical Shaped Semiconductor Integrated Circuit," which is hereby incorporated by reference. Experimental spherical-shaped semiconductor devices or "balls" can be made with diameters of about 1.0 millimeter or smaller. Integrated circuit functions become more limited as diameters decrease, but simple functions that have useful applications can be provided on semiconductor balls of 0.1 millimeter in diameter or smaller. The spherical shape of such devices has density advantages over comparably sized flat semiconductor devices made using conventional wafer fabrication processes. Other advantages can be realized specific applications as revealed by the examples herein.

The miniature electronic device is comprised of a spherical integrated circuit (ball) that is one millimeter or less in diameter with transducer and data communication capabilities. The ball with an integrated sensor can be secured or attached to a catheter, guidewire, stylet, or needle and inserted within body cavities or vascular or other types of spaces. The ball, either singly or in clusters, can sense pressure, flow, velocity, pH, $pO_2$, $pCO_2$, temperature, or measure organic or inorganic molecules or macromolecules. The information is gathered and processed by a ball sensor at the site of the sample, and then transmitted to a central processing unit outside the body for recording and storage. The information transfer can be made through a hard-wired connection or by close-range radio frequency transmission (RF). Under certain conditions, the ball can include a transducer that functions as an actuator, in which case a signal may be transmitted back to the ball where infrared, laser, electrical or ultrasound energy is delivered to a target.

The disclosed architecture allows for measurement of pressure, flow, oxygenation, temperature, pH, $pCO_2$, and $pO_2$ directly, and can be used in body cavities including, but not limited to, intra-abdominal, intrathoracic, joint, and intracranial spaces. Measurements are transmitted to a central processing unit via radio frequency signals during the procedure avoiding any laboratory delay or need for calculations. Moreover, the information can be continuously monitored. The data can also be stored in the on-board central processing unit.

CATHETER AND GUIDEWIRE APPLICATIONS

One application of the present invention is the use of a ball sensor at the tip of a guidewire used in interventional procedures, such as balloon angioplasty for the treatment of atherosclerotic occlusive disease. Miniature semiconductor balls can be provided on the distal segments of catheters and guidewires to sense pressure, flow rate and other parameters. A pressure sensor at the tip of the catheter or the guidewire can measure pressure and flow without losing wire position and without having to exchange catheters. This concept can also be applied to any vascular procedure in which a stenotic lesion is treated or potentially may be treated, whether by balloon angioplasty or any of the various atherectomy techniques. Pressure and flow measurements can be obtained across these lesions to determine if the lesion is physiologically significant and whether dilation has been successful. The current invention can be used in both the arterial and venous vessels including but not limited to the following: coronary, carotid, aorta, renal, hepatic, mesenteric, iliac, femoral, popliteal, tibial, brachiocephalic, subdlavain, jugular, and inferior vena cava, as well as numerous venous and arterial graft sites.

Referring now to FIG. 1, there is illustrated the distal end of a prior art guidewire 10 for use in guiding a catheter (not shown) to the site of a stenosis requiring treatment by balloon angioplasty. Examples of prior art guidewires are disclosed in the following U.S. Pat. No. 4,554,929, entitled "Catheter Guide Wire With Short Spring Tip And Method Of Using The Same," issued Nov. 26, 1985; U.S. Pat. No. 4,884,579, entitled "Catheter Guide Wire," issued Dec. 5, 1989; U.S. Pat. No. 4,886,067, entitled "Steerable Guidewire With Soft Adjustable Tip," issued Dec. 12, 1989; U.S. Pat. No. 5,292,315, entitled "Low Profile Catheter For Increasing Lumen Size Of A Blood Vessel And Guide Wire Therefor," issued Mar. 8, 1994; U.S. Pat. No. 5,365,942, entitled "Guidewire Tip Construction," issued Nov. 22, 1994; U.S. Pat. No. 5,465,733, entitled "Guide Wire For Catheters And Method For Its Use," issued Nov. 14, 1995; and U.S. Pat. No. 5,720,300, entitled "High Performance Wires For Use In Medical Devices And Alloys Therefor," issued Feb. 24, 1998, which are incorporated herein by reference.

The guidewire 10 has a helical coil 12 formed around a core wire 14. The helical coil 12 and core wire 14 terminate in a hemispherical tip or cap 16. The cap 16 is connected to the helical coil 12 and core wire 14 by conventional means, such as by a brazed joint (not shown).

Figure 2A:
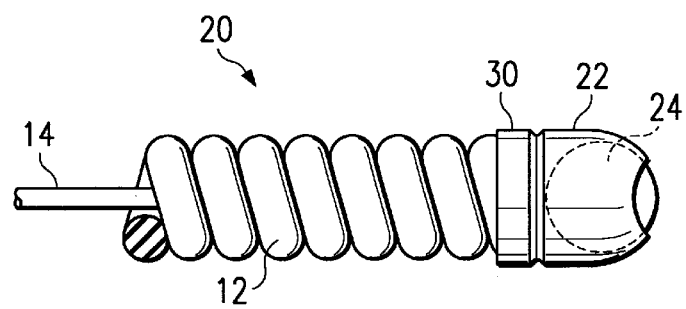
FIG. 2A illustrates a schematic partial end view of a guidewire similar to the guidewire of FIG. 1 but modified to include a ball sensor at the distal end of the guidewire in accordance with a disclosed embodiment.
Figure 2B:
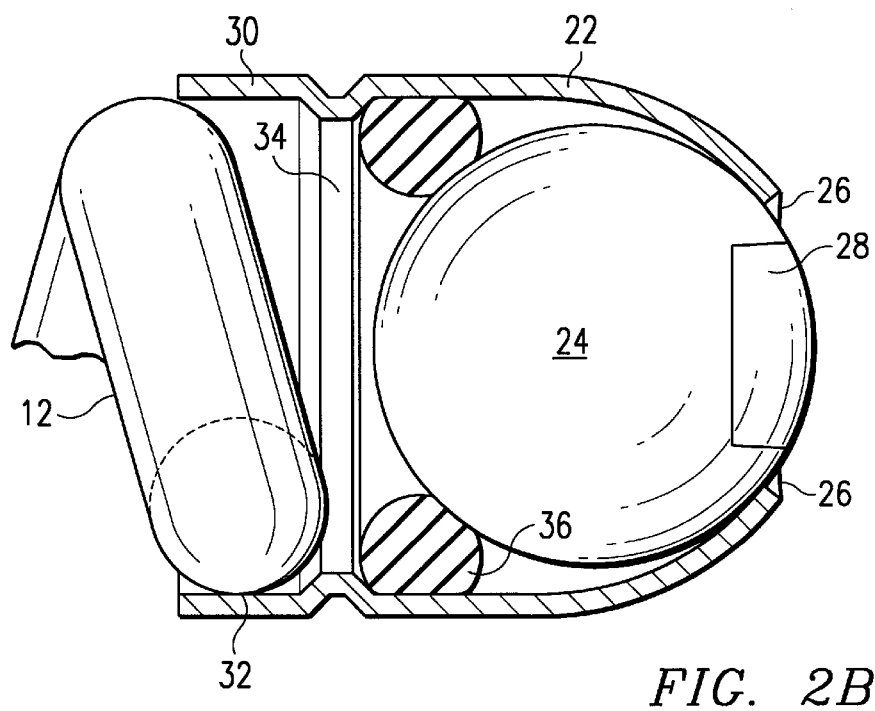
FIG. 2B illustrates an enlarged partial cross section through the end cap of FIG. 2A showing the ball sensor mounted therein.

Referring now to FIG. 2A, there is illustrated the distal end of a guidewire modified in accordance with a disclosed embodiment. The helical coil 12 and core wire 14 may be the same as with the conventional guidewire 10 and therefore, are designated using the same reference numerals. A modified guidewire 20 differs from the prior art in the inclusion of a modified end cap 22 that includes a ball monitor 24 mounted therein. The construction of the end cap 22 is shown in greater detail in the enlarged cross-sectional view of FIG. 2B. The end cap 22 terminates in a circular opening 26 through which a transducer 28 on the surface of the ball 24 extends. The transducer 28 may be a pressure sensor such as described in commonly-assigned U.S. Patent Application entitled "Miniature Spherical-Shaped Semiconductor With Transducer," which is hereby incorporated by reference, and which was filed on the same day as the present application.

The proximal end of the cap 22 has a cylindrical portion 30 that serves as a mounting area within which the distal end of the coil 12 is secured. The coil 12 can be secured in any suitable manner by, for example, soldering at several points, such as at the abutting surface 32. A circumferential rib 34 separates the mounting cylinder 30 from the distal end of the cap 22 that houses the ball sensor 24. The rib 34 also serves to hold a rubber O-ring 36 in place, which in turn resiliently secures the ball sensor 24 within the cap 22. In assembling the guidewire 20, the ball sensor 24 is placed in position shown in the cap 22 by passing it through the mounting cylinder 30 and rib 34. Then, the O-ring 36 is snapped into place. Finally, the coil 12 is soldered to the mounting cylinder 30.

The guidewire 20 with the ball sensor 24 therein can be used to measure the blood pressure in an artery during and/or after angioplasty. The transducer 28 senses pressure and communicates the pressure information to a monitoring station in a manner described in greater detail hereinbelow. It will be appreciated that the transducer 28 may perform other functions as the need dictates and the manufacturing capability permits.

Figure 3:
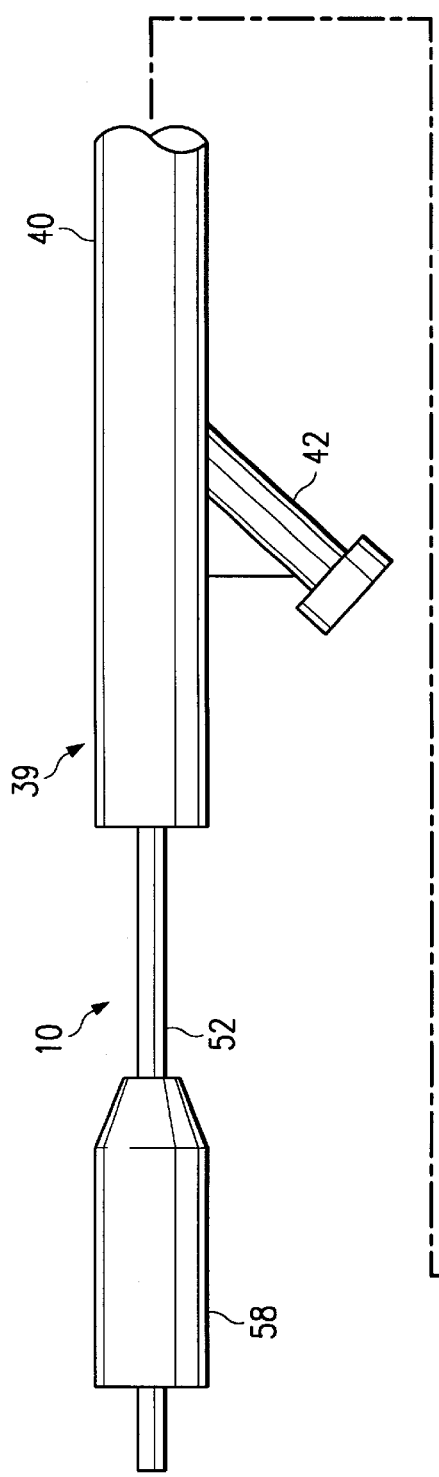
FIG. 3 illustrates a schematic partial side view of a balloon catheter and guidewire of the prior art.
Figure 3:
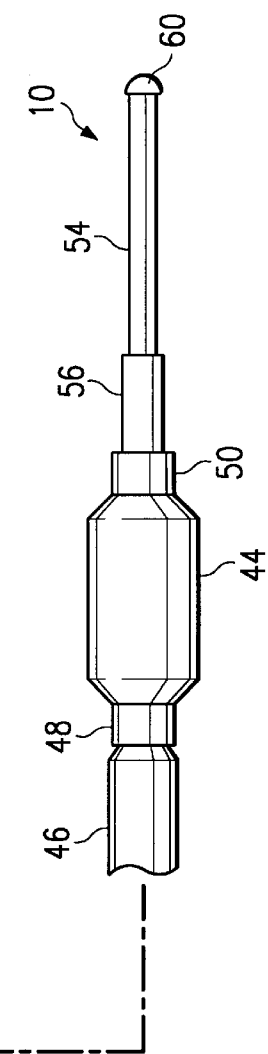

Referring now to FIG. 3, there is illustrated a prior art balloon catheter and guidewire system. The proximal end of the catheter 39 includes a manifold 40 and an inflation port 42. A conventional balloon 44 is affixed to the catheter's distal end 46 at seals 48 and 50. The guidewire 10 includes a proximal end 52 and distal end 54. The distal end 54 of the guidewire 10 is shown emerging from the catheter's distal orifice indicated by reference numeral 56. The guidewire 10 includes a handle 58 at the proximal end and an end cap 60 at the distal end.

Use of such a conventional balloon catheter 39 and guidewire system 10, is well known in the art. Briefly, the guidewire 10 is first fed through an entry point such as the femoral artery, and then through the iliac artery and the aorta to the site of a stenosis in a cardiac artery. The guidewire 10 is passed through the stenosis and then the catheter 39 is fed through the patient's arteries along the guidewire 10 to bring the balloon 44 into the site of the stenosis for treatment. The balloon 44 is inflated by introducing air under pressure through the port 42, which communicates with the balloon 44 through an inflation lumen within the catheter 39. For example, the inflation lumen may be an annulus surrounding the main central lumen of the catheter 39 through which the guidewire 10 passes. Such catheter 39 structures are well known.

Figure 4:
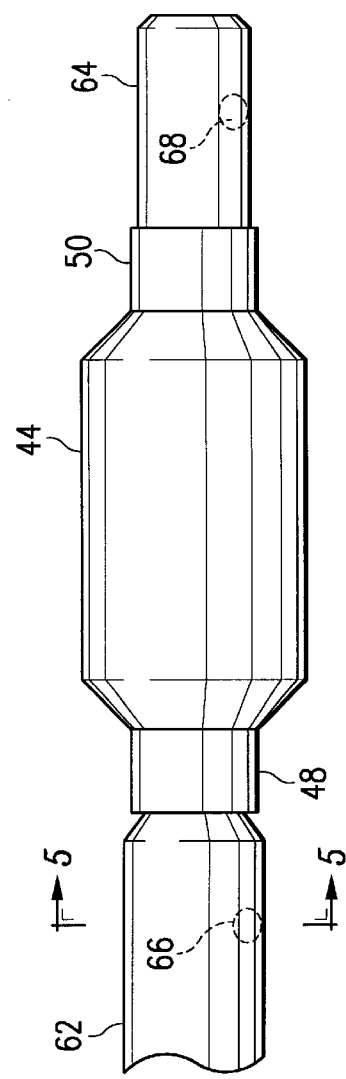
FIG. 4 illustrates an enlarged side view of the balloon portion of the catheter of FIG. 3 modified to include catheter segments with ball monitors mounted therein.

Referring now to FIG. 4, there is illustrated an enlarged side view of the balloon portion of the catheter of FIG. 3 modified to include catheter segments with ball monitors mounted therein. The distal end of the catheter 39 includes the balloon 44 having a proximal collar 62 and a distal collar 64 on opposite sides of the balloon 44. The proximal collar 62 is connected to the balloon at seal 48 and the distal collar 64 is connected to the balloon at seal 50. Ball monitors 66 and 68 are secured within the walls of the collars 62 and 64, respectively.

Figure 5:
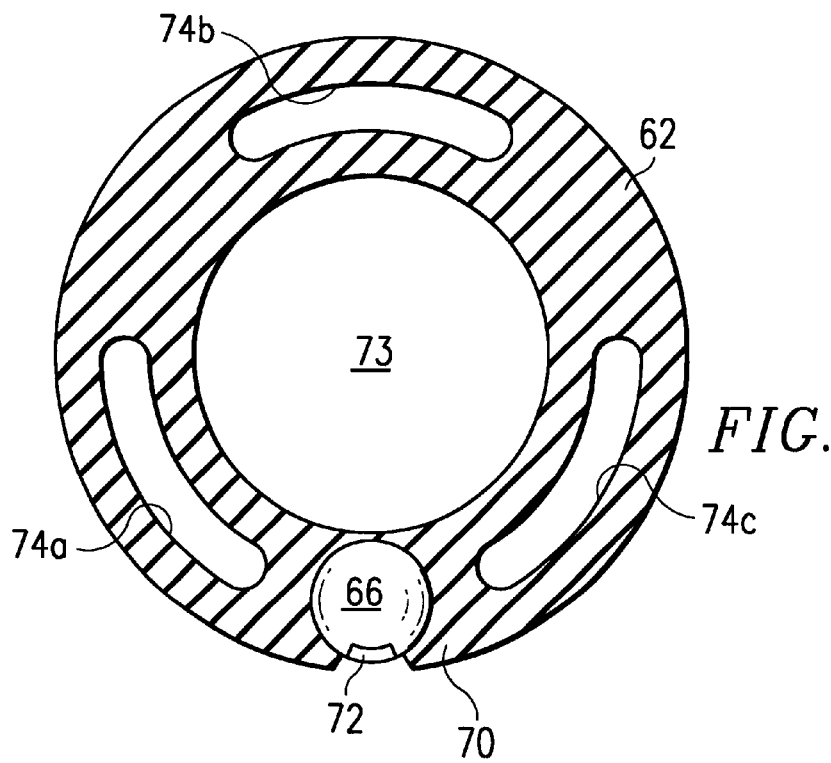
FIG. 5 illustrates an enlarged cross section taken along line 5—5 of FIG. 4.

Referring now to FIG. 5, there is illustrated an enlarged cross section taken along line 5—5 of FIG. 4 depicting the manner in which ball 66 is secured within the wall 70 of the collar 62. The ball 66 includes a pressure sensor 72 in communication with the space within the patient's artery surrounding the collar 62 by means of an opening in the wall 70 at the bottom immediately below the ball 66, as shown. The collar 62 has a central lumen 73 through which the guidewire passes. Annular passageways 74a, 74b, and 74c provide the means for inflating the balloon 44 by a pressurized air source (not shown) that is in communication with the annular passageways through the previously described port 42. The portion of the catheter 39 within the balloon 44 has openings (not shown) in communication with the annular passageways 74a, 74b, and 74c. Since these passageways terminate within the balloon 44, the collar 64 can have a thinner wall than the collar 62, and therefore can have a slightly smaller outside diameter.

The ball sensor 66 can sense the pressure in the artery at a point proximal to the stenosis during angioplasty. Similarly, the ball 68 shown in FIG. 4, is mounted in the wall of the collar 64, and thus communicates with the blood in the lumen of the artery at a point distal from the stenosis. It will be appreciated that the two separate pressure readings from the balls 66 and 68 on opposite sides of the balloon 44 at the site of a stenosis can provide very helpful information to the physician during the procedure. The ball sensors 66 and 68 can measure pressure proximally and distally to the stenotic lesion, and document any pressure drop across the lesion. After balloon angioplasty, the pressure differential across the lesion should have been resolved and the pressures in the proximal and distal balls (66 and 68, respectively) should be equal. Communication of pressure data from the ball sensors 66 and 68 to an exterior monitoring station preferably uses RF transmissions, as will be described hereinbelow.

Figure 6:
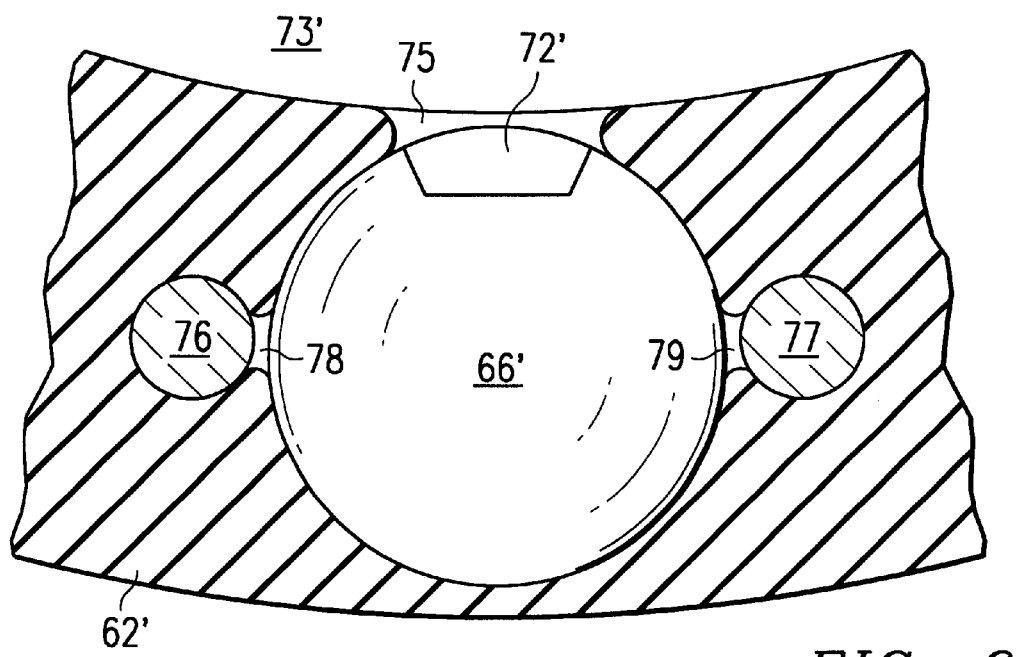
FIG. 6 illustrates an enlarged cross section through a catheter sidewall showing an alternative embodiment.

Referring now to FIG. 6, there is illustrated an enlarged cross section through a catheter sidewall of an alternative embodiment. A ball sensor 66' is secured within the wall 62' of a catheter. In this example, however, the ball 66' includes a transducer 72' in communication with the central lumen 73' of the catheter through an opening 75. As an alternative to the RF communication system previously mentioned in connection with the ball sensor 66 of FIG. 5, the ball 66' is connected to communicate through wires 76 and 77 with a data processing station located outside the patient's body. The wires 76 and 77 are embedded in the wall 62' of the catheter and extend out to the data processing station. Connections between the ball 66' and the wires 76 and 77 can be made through solder connections 78 and 79, respectively. The wires 76 and 77 can have reduced diameter portions at the point of making the solder connections 78 and 79 so that current can be passed through the wires to cause localized heating and affect good solder joints at connection points 78 and 79.

In operation, wire 76 can provide a positive power source to the ball 66, such as 3.0 volts, and wire 77 can provide a ground connection. Data communication with the ball 66' can be by analog signals superimposed on the positive supply line 76. Alternatively, digital data communication can be effected by asynchronous serial transmission using a bit-by-bit communications protocol. For example, to communicate a "one" bit, the voltage on wire 76 can be pulled low and then released after a short duration, followed by a test window. A "zero" bit can be transmitted by pulling the voltage on wire 76 low and holding it at the low logic level for a duration that extends through the test window time period. Such communication systems are well known in the art. Communicating by such a wired system with the ball 66' reduces the complexity of the circuitry on the ball, since it is not necessary to include a power receiving coil, an RF transmission coil, and the associated circuitry.

It will be appreciated that catheter applications other than for balloon angioplasty can be implemented using the miniature ball sensors described above. For example, in catheters with side holes used for introducing fluids into vessels, ball sensors can be attached adjacent to the side holes for monitoring various conditions. These open holes can be used for irrigation of fluid, drug delivery, or for introducing contrast fluids. In catheters that do not have an open end, a ball sensor can be attached to the tip of the catheter for pressure sensing or other transducer functions.

Figure 7:
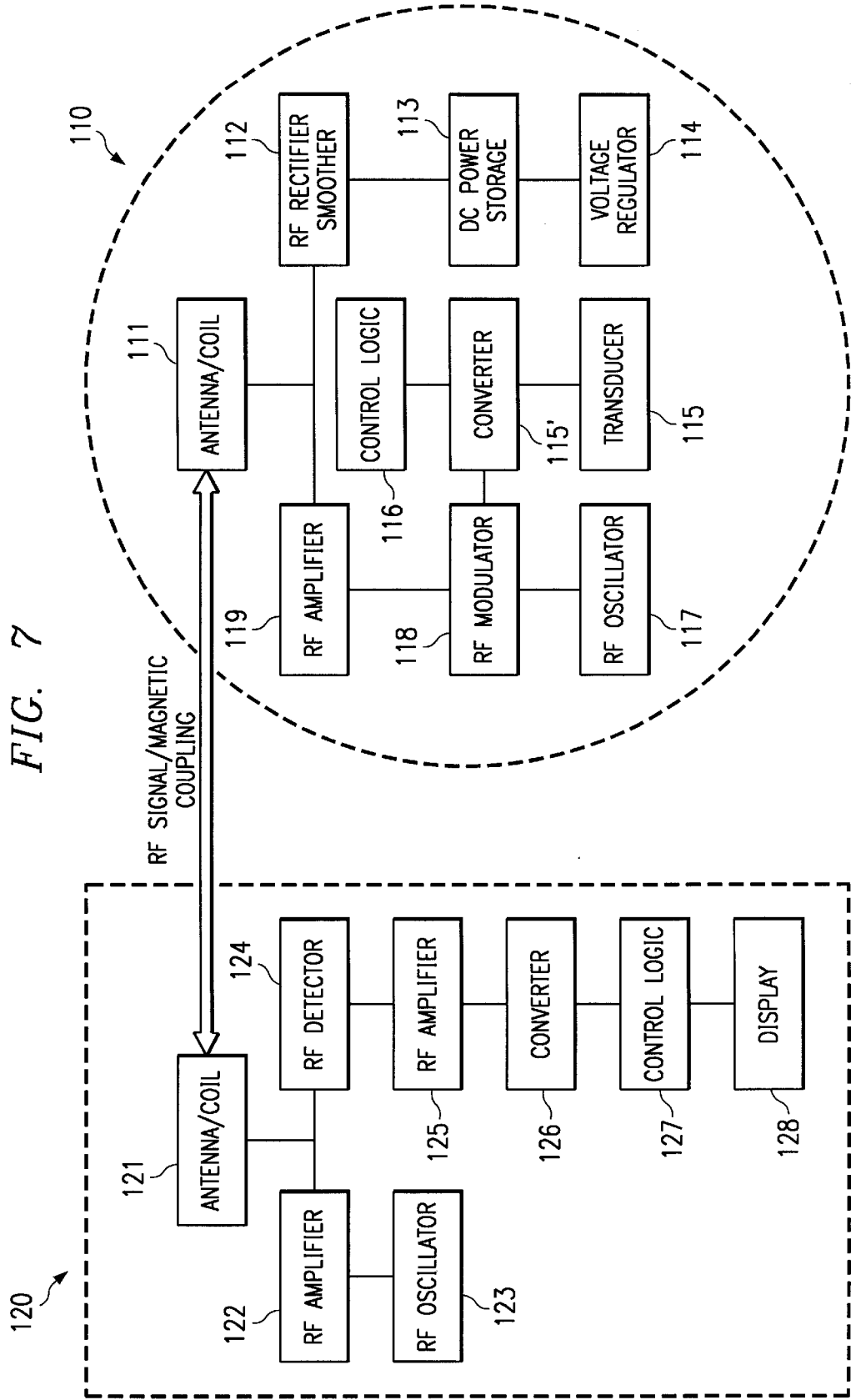
FIG. 7 illustrates a block diagram of a ball with an integral transducer in combination with an RF communication system.

Referring now to FIG. 7, there is illustrated a block diagram of a ball with an integral transducer in combination with an RF communication system. The basic circuit functions performed by a semiconductor ball are designated generally by reference numeral 110, which communicates with a monitoring station designated generally by reference numeral 120.

The ball 110 includes an antenna/coil 111, which serves the dual purpose of receiving power from the station 120 and transmitting data on an RF carrier signal to the station 120. The power may be received by the antenna/coil 111 by direct magnetic coupling, if the station 120 is sufficiently close to the ball 110. Alternatively, an electromagnetic wave can be used to transmit power from the station 120 to the ball 110, whereby the magnetic field component of the electromagnetic wave induces a current in the coil 111 in accordance with known techniques. The power signal received by the antenna/coil 111 is rectified and smoothed by an RF rectifier smoother circuit 112. The output of the rectifier circuit 112 is connected to a DC power storage device 113, such as a capacitor. Such capacitor might also perform the waveform smoothing function. A voltage regulator 114 is used to make the DC voltage stable regardless of the distance between the station 120 and the ball 110. For example, a Zener diode or other suitable clamping circuit can perform this function. The resulting DC voltage is supplied to all circuits of the ball 110.

The ball 110 includes at least one transducer 115, which may be a sensor or an actuator. In the case of a sensor, a condition or parameter of the environment in which the ball is located is sensed. For example, pressure can be sensed through a change in capacitance or resistance. Such semiconductor pressure transducers are known in the art and can be adapted to fabrication on a spherical semiconductor substrate. A variable-resistance strain gauge is disclosed in commonly-assigned U.S. Patent Application entitled "Intraluminal Monitoring System," which is hereby incorporated by reference, and which was filed on the same date as the present application.

A converter 115', which may be an analog-to-digital (A/D) converter, is used to convert the condition sensed by the transducer 115 to a signal that can be transmitted out to the station 120. The converter 115' can be part of the transducer 115, such as a variable capacitor for generating a signal depending upon the variations in capacitance. Control logic 116, which can be part of an on-board processor that controls not only the converter 115', but also other circuitry on the ball 110, is provided in accordance with known techniques.

An RF oscillator 117 generates an RF carrier signal at a predetermined frequency in the RF band. An RF modulator 118 modulates the output of the converter 115' onto the carrier frequency signal. The resulting modulated signal is amplified by RF amplifier 119, and then transmitted to the outside through the antenna/coil 111. Further details of the preferred coil are described in the aforementioned commonly assigned U.S. Patent Application entitled "Miniature Spherical-Shaped Semiconductor With Transducer."

The monitoring station 120 includes an antenna/coil 121 that serves the dual purpose of generating the electromagnetic wave for transmitting power to the ball 110, and receiving the RF data signal transmitted by the ball 110. It is preferred that the frequency of the electromagnetic wave that is output by the antenna/coil 121 is different from the carrier frequency generated by the RF oscillator 117. An RF amplifier 122 is used to couple the electromagnetic wave for power transmission to the antenna/coil 121. RF oscillator 123 determines the frequency of the electromagnetic wave that is emitted by the station 120. The data signal received by the antenna/coil 121 is detected by an RF detector 124 and then amplified by an RF amplifier 125. Preferably, the converter 126 converts the signal from the RF amplifier 125 to a digital signal, which in turn is input to control logic 127. The control logic 127 may be a special purpose central processing unit (CPU) an interface to a general purpose CPU or computer. The control logic 127 extracts the data from the signal received by the station 120 from the ball 110 and displays that information on a suitable display 128, such as a CRT screen. The technique for transmitting data from the ball 110 to the station 120 using the carrier frequency generated by the RF oscillator 117 can be in any form using any suitable protocol. The modulation can be AM, FM, PM or any other suitable modulation technique.

Figure 8:
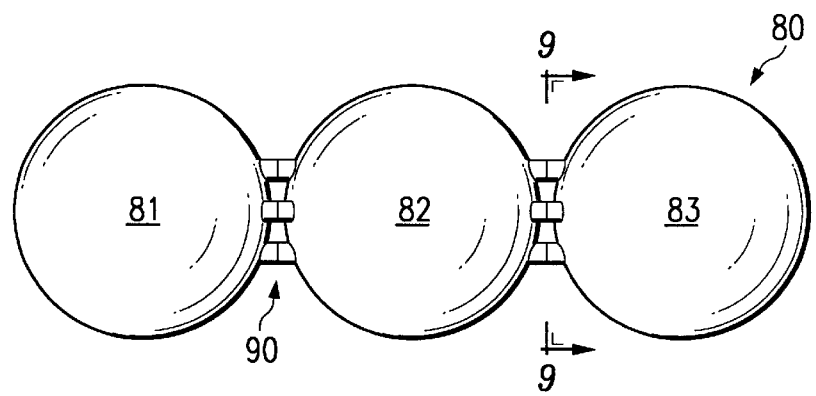
FIG. 8 illustrates a side elevation of a cluster of semiconductor balls that may be employed in a transducer function.

Referring now to FIG. 8, there is illustrated a side elevation of a cluster of semiconductor balls that may be employed in a transducer function. Although a single ball can include the foregoing functions, more complex monitoring functions with multiple transducers can be implemented using multiple ball systems attached to catheters, needles and other insertable devices. For example, ball 81 can include power receiving and data transmission functions. Alternatively, ball 81 can be a miniature ball-shaped battery. Ball 82 can include a first transducer function, such as pressure sensing, and ball 83 can include a second transducer function, such as measuring pH, $pO_2$, $pCO_2$, or temperature, as the particular application requires. Connections between the balls are made through metal contacts 90, which may be solder bumps.

Figure 9:
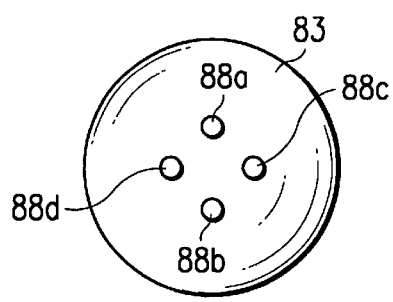
FIG. 9 illustrates a cross section along a line 9—9 to expose electrical contacts between two connected balls.

Referring now to FIG. 9, there is illustrated a cross section taken along the line 9—9 of FIG. 8 to expose the four contacts 88a, 88b, 88c and 88d between ball 82 and ball 83. The contacts 88a and 88b may be power contacts, such as a positive 3.0 volts and ground, which can be passed from ball 81 around ball 82 by conductors on its surface using two of a group of similar contacts (designated collectively by numeral 90 in FIG. 8). The contacts 88c and 88d may be data and control contacts for communications between ball 82 and ball 83. Similar data and control contacts may exist among contact group 90 between ball 81 and ball 82 to the extent needed.

Figure 10:
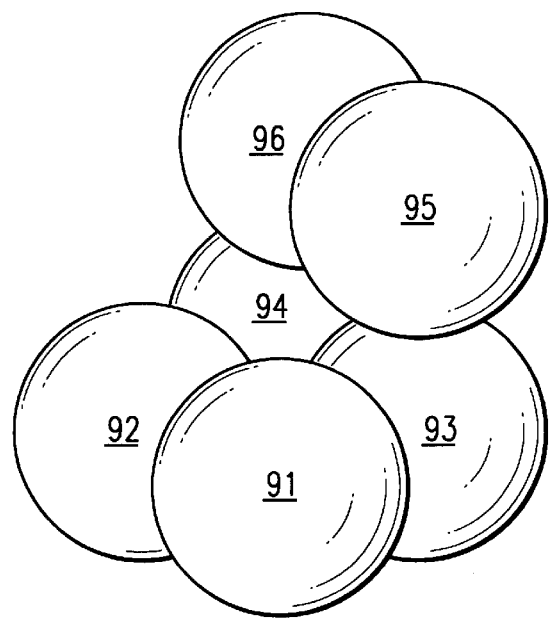
FIG. 10 illustrates a schematic depiction of a cluster of semiconductor balls that may have application in the context of a disclosed embodiment.

Referring now to FIG. 10, there is illustrated a cluster of balls 91, 92, 93, 94, 95 and 96 as an example of the versatility of such ball systems. The cluster specifically shows six balls arranged in a three-dimensional configuration. It will be appreciated that various other cluster arrangements are possible, limited only by the constraints of the end-use application. Each of the balls of the cluster can perform different electronic functions and communicate with each other through contacts as described above in connection with FIGS. 8 and 9. For example, ball sensors are located on the sides of catheters and can measure various parameters. Clustered balls are able to integrate, transmit, and receive more complex information or actuate a response (emit laser, infrared, ultrasound, or electrical energy). The actuators may contain a piezoelectric driver attached to a ball surface for ultrasound generation and control for measurements of luminal diameter and fluid flow rate within the vessel lumen. Such actuators can serve as an emitting device allowing for external detection to determine location or position.

NEEDLE AND STYLET APPLICATIONS

Ball sensors can also be used effectively on needles and other insertable instruments for more accurate measurement of internal body conditions. For example, needles are often inserted into vascular and other body fluid compartments to either inject or remove fluids. Pressure, pH, $pO_2$, $pCO_2$, glucose and protein measurements are frequently required and can be obtained while the needle is indwelling. In this procedure, a needle is inserted into a blood vessel or fluid compartment. A pressure and/or chemical sensor(s) contained on the ball(s) situated on the tip of the needle, luminal surface of the needle chamber or within IV tubing monitors pressure directly and continuously during the entire indwelling period. This may be particularly beneficial in hemodialysis patients where needles are indwelling for three to four hours during treatments. Changes in venous or arterial pressures over multiple hemodialysis sessions may signify the development of arterial or venous anastamotic strictures within the graft prior to complete blockage. Corrective measures such as angioplasty, stent placement or surgical excision may be performed prior to the development of complete graft failure. This obstructive process continues to be a major cause of dialysis patient morbidity. The needle may also be inserted into other body cavities for sampling or pressure measurement. These needles are used but are not limited to the following procedures: lumbar puncture, joint aspiration, paracentesis, and thoracocentesis.

Figure 11:
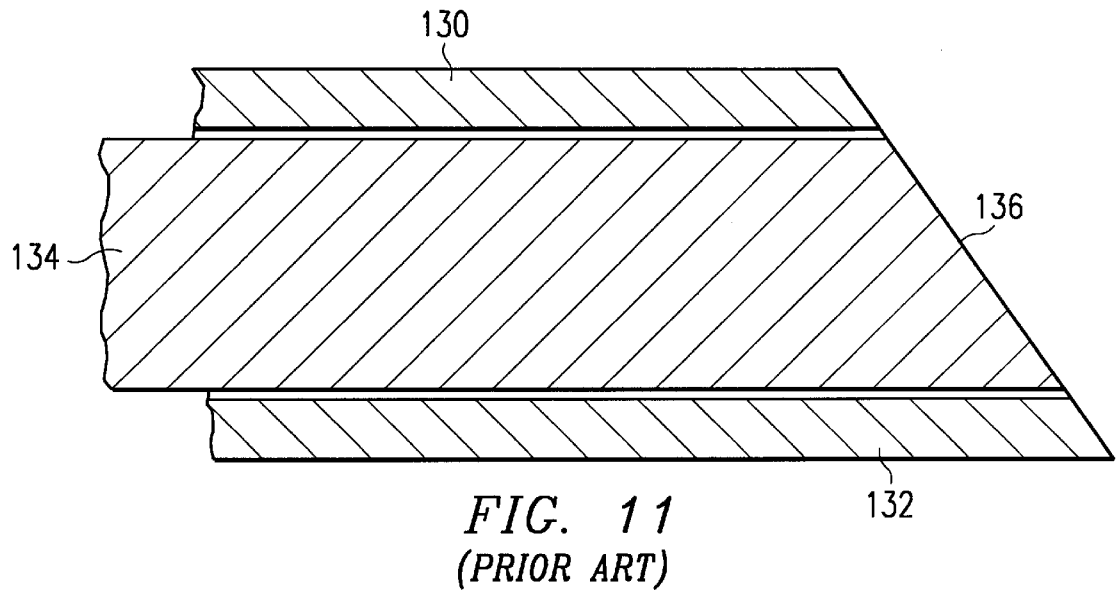
FIG. 11 illustrates an enlarged cross section of the distal ends of a needle and stylet of the prior art.

Referring now to FIG. 11, there is illustrated a cross section of a prior art needle and stylet. The distal end of a needle 130 is shown having a sharp point 132 to facilitate passing through tissue, as in the case of a spinal tap procedure. To prevent tissue from being drawn into the lumen of the needle 130, a stylet 134 is inserted into the needle 130. The stylet 134 has an angled face 136 that is flush with the distal edge of the needle 130. Ordinarily, after insertion of the needle 130 and stylet 134 in tandem into the spinal cavity, the stylet 134 is withdrawn to permit access to the spinal fluid through the needle 130.

Figure 12:
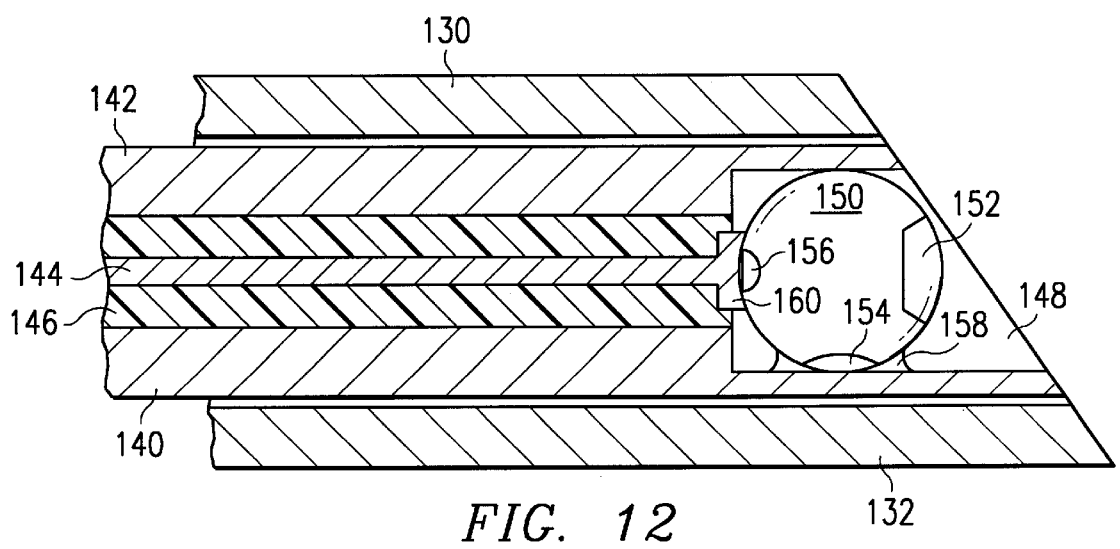
FIG. 12 illustrates an enlarged cross section of a needle and stylet modified to include a ball transducer according to a disclosed embodiment.

Referring now to FIG. 12, there is illustrated an enlarged cross section of a needle and stylet modified to include a ball sensor. After insertion of the needle 130 and stylet 134 into the spinal cavity as described above, the stylet 134 is withdrawn and a specially modified stylet 140 is inserted into the lumen of the needle 130 to the position shown in FIG. 12. The modified stylet 140 has a metal annulus 142 extending throughout its length and a communication wire 144 axially disposed therein. The wire 144 is surrounded by an insulator 146 to electrically isolate it from the stylet 140. A recessed cavity 148 is provided at the distal end of the stylet 140 to accommodate a ball device 150. A transducer 152, such as a pressure sensor, is integrated on the ball 150, together with other circuitry, on an internal spherical semiconductor substrate. The ball 150 has a ground terminal 154 and a data terminal 156. The ground terminal is electrically connected to the metal annulus of the stylet 140 by a solder joint 158. The data contact 156 is connected to the communication wire 144 by a contact 160.

In operation, the transducer 152 senses the pressure of the fluid in the body cavity in which the needle 130 has been inserted. The pressure can be transmitted to an external monitoring station in a suitable manner, such as by an analog signal on the wire 144. As an alternative, the wire 144 can be eliminated and an RF communication system substituted, such as has been described above in connection with FIG. 7. Any of various protocols for communicating with the ball 150 can be implemented. Of course, the example of FIG. 12 is just one of many possible implementations of an interventional procedure applying the principles of the present embodiment. Other applications as outlined hereinabove or as may occur to the skilled practitioner, are within the scope of the disclosure.

Figure 13:
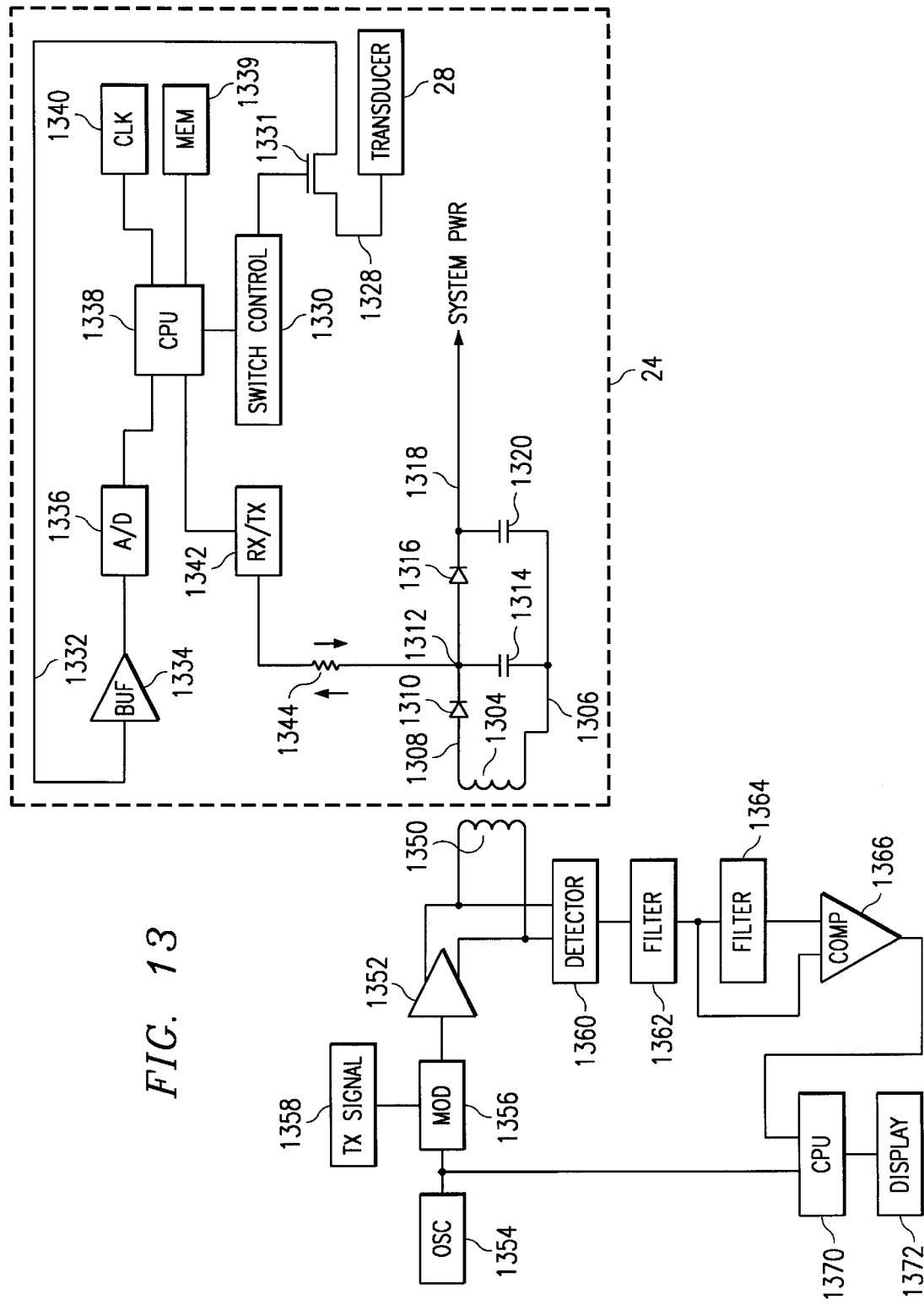
FIG. 13 illustrates a schematic block diagram of the receiver/transmitter and a detection/power system according to a disclosed embodiment.

Referring now to FIG. 13, there is illustrated a schematic block diagram of the monitor and the remote system for the powering/detection operation illustrated in FIG. 7. The ball sensor 24, as described hereinabove, is operable to provide the transducer 28 for interfacing with the desired quantitative condition. The illustrated embodiment of FIG. 13 is that associated with a "passive" system, which term refers to a system having no battery associated therewith. In order to operate the system, there is provided an inductive coupling element 1304 in the form of an inductor, which is operable to pick up an alternating wave or impulse via inductive coupling, and extract the energy therein for storage in the inductive element 1304. This will create a voltage across the inductive element 1304 between a node 1306 and a node 1308. A diode 1310 is connected between the node 1308 and the node 1312, with the anode of diode 1310 connected to node 1308 and the cathode of diode 1310 connected to a node 1312. Typically, the diode 1310 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 1310 is operable to rectify the voltage across the inductive element 1304 onto the node 1312, which has a capacitor 1314 disposed between node 1312 and node 1306. Node 1312 is also connected through a diode 1316 having the anode thereof connected to node 1312 and the cathode thereof connected to a node 1318 to charge up a capacitor 1320 disposed between node 1318 and 1306. The capacitor 1320 is the power supply capacitor for providing power to the ball sensor 24. The capacitor 1314, as will be described hereinbelow, is operable to be discharged during operation of the system and, therefore, a separate capacitor, the capacitor 1320, is required for storing power to power the system of the ball sensor 24.

There is also provided a switching transistor 1331 which has one side of the gate/source path thereof connected to a node 1328, which is the output of the transducer 28 and the other side thereof connected to a node 1332. The gate of transistor 1331 is connected to the output of the switch control 1330. Node 1332 is connected to the input of a buffer 1334 to generate an analog signal output thereof which is then converted with an analog-to-digital converter 1336 to a digital value for input to a CPU 1338. The CPU 1338 is operable to receive and process this digital input voltage. A clock circuit 1340 provides timing to the system. A memory 1339 is provided in communication with the CPU 1338 to allow the CPU 1338 to store data therein for later transmittal back to the remote location or for even storing received instructions. This memory 1339 can be volatile or it can be non-volatile, such as a ROM. For the volatile configuration, of course, this will lose all information when the power is removed. The CPU 1338 is operable to provide control signals to the switch control 1330 for turning on the transistor 1331 at the appropriate time. In addition to the transistor 1331 being toggled to read the transducer 28, transistor 1331 could be a pass-through circuit such that the CPU 1338 can continually monitor the voltage at the output of the transducer 28. System power to all power-consuming elements of the ball sensor 24 is provided at the SYSTEM PWR output node.

In order to communicate with the CPU 1338 for transferring data thereto and for allowing the CPU 1338 to transfer data therefrom, a receive/transmit circuit 1342 is provided for interfacing to node 1312 through a resistive element 1344. This allows RF energy to be transmitted to node 1312. It is important to note that the semiconductor junction across diode 1310 is a capacitive junction. Therefore, this will allow coupling from node 1312 to node 1308. Although not illustrated, this could actually be a tuned circuit, by selecting the value of the capacitance inherent in the design of the diode 1310. In any event, this allows an RF connection to be provided across diode 1310 while allowing sufficient energy to be input across conductive element 1304 to provide a voltage thereacross for rectification by the diode 1310 and capacitor 1314. Typically, the frequency of this connection will be in the MHz range, depending upon the design. However, many designs could be utilized. Some of these are illustrated in Beigel, U.S. Pat. No. 4,333,072, entitled "Identification Device," issued Jun. 1, 1982, and Mogi et al, U.S. Pat. No. 3,944,982, entitled "Remote Control System For Electric Apparatus," issued Mar. 16, 1976, which are incorporated herein by reference. With these types of systems, power can continually be provided to the node 1312 and subsequently to capacitor 1320 to allow power to be constantly applied to the ball sensor 24.

A remote system 120 which is disposed outside of the body and proximate to the ball sensor 24 includes an inductive element 1350 which is operable to be disposed in an area proximate to the skin, yet exterior to the body, in the proximity of the ball sensor 24. The inductive element 1350 is driven by a driving circuit 1352 which provides a differential output that is driven by an oscillator 1354. This will be at a predetermined frequency and power level necessary to couple energy from inductive element 1350 to inductive element 1304. Since this is an external system, the power of the oscillator can be set to a level to account for any losses through the body tissues. To allow information to be transmitted, a modulation circuit 1356 is provided which is modulated by a transmitter signal in a block 1358 that allows information to be modulated onto the oscillator signal of the oscillator 1354, which oscillator signal is essentially a "carrier" signal. However, it should be understood that the information that is transmitted to the ball sensor 24 could merely be date information, whereas the CPU 1338 could operate independent of any transmitted information to provide the correct timing for the output pulses and the correct waveshape therefor.

Alternatively, entire control of the system could be provided by the transmit signal 1358 and the information carried thereon, since power must be delivered to the illustrated embodiment due to the lack of any independent power in the ball sensor 24. Note also that the distance of the remote system 120 to the ball sensor 24 may need to be varied such that the power signal coupled to the sensor 24 is of sufficient energy to receive an RF signal back from the sensor 24. The strength of the signals exchanged between the sensor 24 and the remote system 120 varies according to the number of tissues and body parts between the sensor 24 and the remote system 120. For example, where a sensor 24 is introduced in a vein close to the surface of the skin, the signal strength is less likely to be affected since the remote system 120 can be placed very closely to the sensor 24. On the other hand, where the sensor 24 is introduced into an artery near the heart, the signal strength of the remote system 120 may need to be increased to power the monitor 110 having the on-board sensor 24. Alternatively, where the power output of the remote system 120 is limited, the remote system 120 may need be inserted into the body to come into closer proximity of the monitor system 110.

When the information is received from the ball sensor, it is superimposed upon the oscillator signal driving the inductive element 1350. This is extracted therefrom via a detector 1360 which has the output thereof input to a first low pass filter 1362, and then to a second low pass filter 1364. The output of low pass filters 1362 and 1364 are compared using a comparator 1366 to provide the data. The filter 1362 provides an average voltage output, whereas the filter 1364 provides the actual digital voltage output. The output of the comparator 1366 is then input to a CPU 1370 which also is powered by the oscillator 1354 to process the data received therefrom. This can then be input to a display 1372.

Note that the transducer 28 may be replaced with an actuator apparatus such that a stimulus may be applied to the body tissue, as opposed to the reading of quantitative data with the transducer 28, as discussed in detail hereinabove. In this scenario, an actuator signal may need to be coupled into the ball sensor 24, in addition to the power to power the sensor 24 circuitry. The actuator signal then causes the CPU 1338 to control the switch control 1330 to engage the actuator to stimulate the tissue.

Figure 14A:
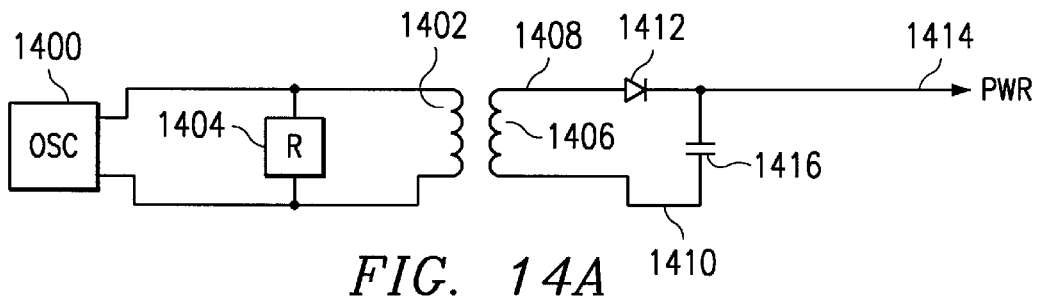
FIGS. 14A–14C illustrate alternative embodiments for the receiver/transmitter and the storage capacitors associated therewith.
Figure 14B:
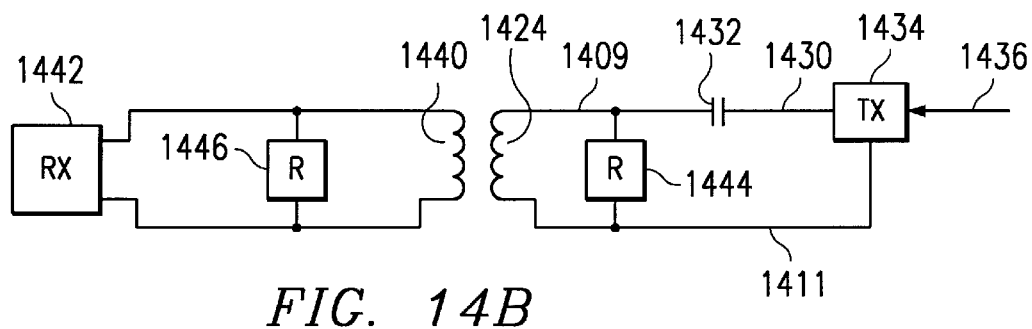
Figure 14C:
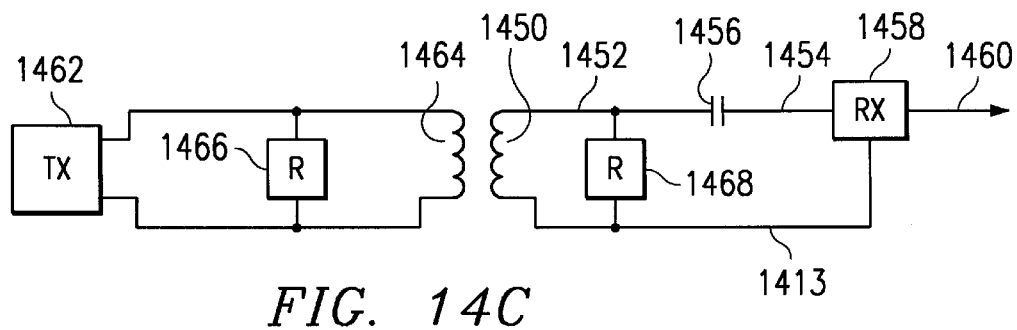

Referring now to FIGS. 14A–14C, there are illustrated alternate embodiments for the transmit/receive operation. In FIG. 14A, there is provided an oscillator 1400 which drives an external inductive element 1402. Typically, there is some type of load 1404 disposed across the inductive element 1402. This is the primary power that is provided to the system. A separate inductive element 1406 is provided on the ball sensor, for being inductively coupled to the inductive element 1402. Thereafter, a voltage is generated across the inductive element 1406, the inductive element 1406 being connected between nodes 1408 and 1410. A diode 1412 is connected between node 1408 and a power node 1414, and a power supply capacitor 1416 is disposed across node 1414 and a node 1410. This allows the voltage on node 1408 to be rectified with diode 1412.

In FIG. 14B, the receive operation, in this alternative embodiment, utilizes a separate inductive element or antenna 1424 in the ball sensor 24, which is operable to be connected between nodes 1409 and 1411. Node 1409 is capacitively coupled to a transmit node 1430 with a capacitor 1432, the capacitor 1432 being a coupling capacitor. A transmitter 1434 is provided for transmitting received data from a line 1436 to the node 1430, which is then coupled to the node 1409 to impress the RF signal across the inductive element 1424.

A corresponding inductive element 1440 is disposed on the external remote controller of remote location 120, which inductive element 1440 is operable to be disposed proximate to the inductive element 1424, but external to the human body. The inductive element 1440 is basically a "pick-up" element which is operable to receive information and function as an antenna, and provide the received signal to a receiver 1442. The structure of FIG. 14B is a separate structure, such that node 1409 is isolated from node 1408, the power receiving node. However, it should be understood that any harmonics of the oscillator 1400 would, of course, leak over into the inductive element 1406. This can be tuned out with the use of some type of tuning element 1444 on the ball sensor 24 disposed across inductive element 1424, and also a tuning element 1446 disposed across the inductive element 1440, i.e., the antenna.

Referring now to FIG. 14C, there is illustrated a simplified schematic diagram of the receive portion. The ball sensor 24 has associated therewith a separate receive antenna or inductive element 1450 disposed between node 1413 and a node 1452. Node 1452 is capacitively coupled to a receive node 1454 with a coupling capacitor 1456. A receiver 1458 is provided for receiving the information transmitted thereto and providing on the output thereof data on a data line 1460. The receiver 1458 is operable to receive the RF signal, demodulate the data therefrom, and provide digital data on the output 1460. External to the human body and the ball sensor 24 is a transmitter 1462 which is operable to impress a signal across an external inductive element 1464. The inductive element 1464 basically provides the RF energy and is essentially tuned with a tuning element 1466. A corresponding tuning element 1468 is provided on the ball sensor 24 and disposed across inductive element 1450, the inductive element 1450 acting as an antenna, as well as the inductive element 1464.

Note that in circumstances where the signals of the ball sensor 24 cannot be adequately received therefrom and/or power coupled thereto, the external location circuitry 120 may need to be inserted into the body proximate to the ball sensor 24 in order to couple the transmit/receive signals and power. Furthermore, where more than one sensor ball 24 is used, communication of power and data signals between the various ball sensors 24 may need to employ distinct time periods (i.e., time multiplexing) when communication occurs using a single common frequency, or discrimination circuits may need to be used where communication occurs simultaneously with the plurality of implanted ball sensors 24 having different oscillator frequencies.

Figure 15:
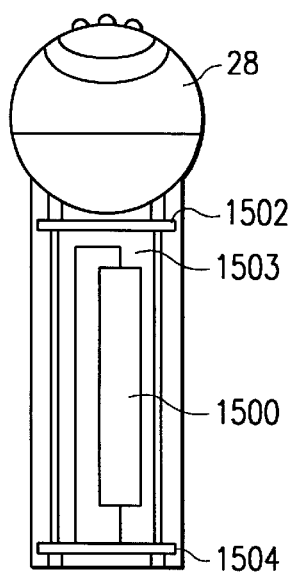
FIG. 15 illustrates a cross-sectional side view of the monitor in an alternate embodiment utilizing a local power source.

Referring now to FIG. 15, there is illustrated a side view of an alternative embodiment utilizing additional circuitry or structure attached to the ball sensor 28 for providing a local power source. As described hereinabove, the ball sensor 28 requires a power-generating structure for storing a power supply voltage such that diodes must be provided for receiving and rectifying a large amount of power and charging up a power supply capacitor. Alternatively, the ball sensor could be configured to interface to an attached power supply system 1500 comprising either a battery or a capacitor. The local power supply system 1500 is illustrated as disposed on a circuit board 1503 defined by supporting structures 1502 and 1504. The circuit board 1503 contains electronics for interfacing the local power supply system 1500 to the ball sensor 28.

Figure 16:
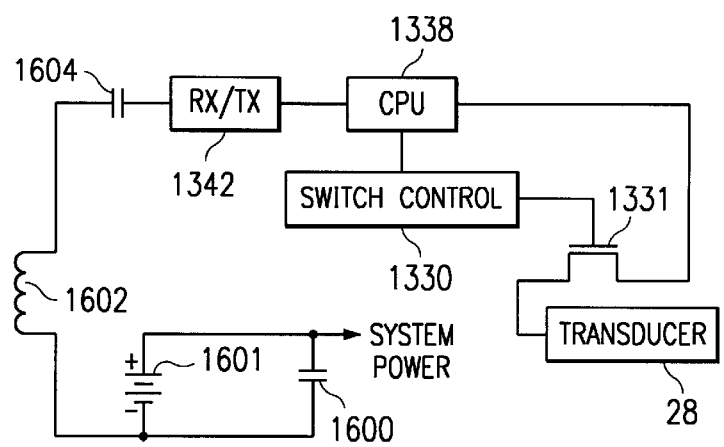
FIG. 16 illustrates a schematic block diagram of the circuitry utilizing a battery as the primary power source.

Referring now to FIG. 16, there is illustrated a schematic block diagram of the ball sensor 24 using a battery as the local power supply system 1500. A battery 1601 is provided as a source of self-contained power and is connected across a capacitor 1600 to providing smoothing of any power output to the system power-consuming elements of the ball sensor 24. Power for all on-board components is obtained from the SYSTEM POWER output by providing sufficient charge to the capacitor 1600. The capacitor 1600 could be formed on the surface of the ball sensor 24 or it could actually be part of the battery structure 1601. Additionally, the capacitance 1600 could actually be the capacitance of the battery 1601. Additional structure could be provided for powering the CPU 1638 and the other circuitry on the ball sensor 24 from the battery 1601. As such, there would only be required a smaller inductive element 1602 and a capacitor 1604 to allow the receive/transmit block 1342 to receive/transmit information from and to the remote exterior station 120. The switch control 1330 controls the gate of the switching transistor 1331 to switch output of the transducer 28 through the switching transistor 1331 source/drain path to the CPU 1338.

Figure 17:
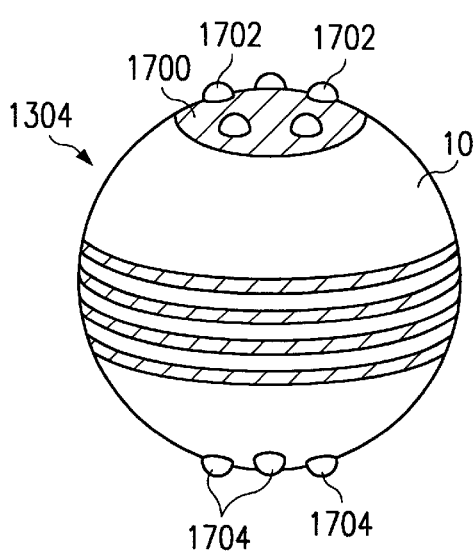
FIG. 17 illustrates a perspective view of one of the spherical semiconductor monitors having the antenna leads disposed thereon.

Referring now to FIG. 17, there is illustrated a perspective view of a ball sensor 10, wherein the inductive element 1304 (inductive element 1602 being similar thereto) is illustrated as being strips of conductive material wrapped around the exterior of the ball sensor 10. The inductive element 1304 is formed of a conductive strip wrapped many times around the ball sensor 10. The length of inductive element 1304 depends upon the receive characteristics that are required. As described hereinabove with reference to FIGS. 14A–14C, there could be multiple conductive strips, each associated with a receive function, a transmit function or a power function, or they could all share one single conductive element or strip. On one end of the ball sensor 10 there is provided a transducer interface 1700 of the transducer 28 having, optionally, one or more interface balls 1702 (or partial balls, called nodules) associated therewith extending from the transducer interface surface to provide enhanced engagement of the measuring surface or physical entity. The interface balls 1702 can be made of non-reactive material, e.g., gold to prevent degradation while in the body. Note that in some applications, the interface nodules 1702 are not required for obtaining the desired quantitative data. On the other end of the ball sensor 10 are provided interconnect balls 1704 (or nodules) for interconnecting to one or more other spherical balls which may provide similar functions such as monitoring of quantitative data, or unique functions such as supplying only power or data buffering and storage.

Figure 18:
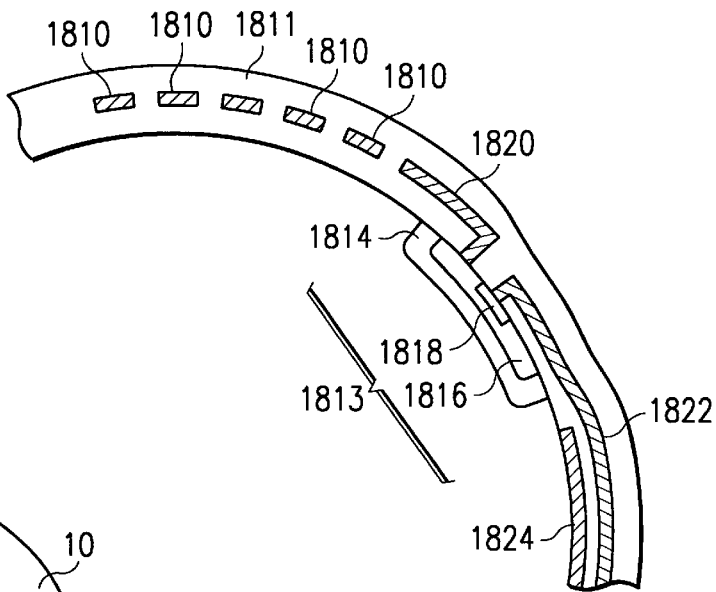
FIG. 18 illustrates a cross-sectional diagram of the portion of the surface of the spherical monitor ball of FIG. 17.

Referring now to FIG. 18, there is illustrated a cross-sectional diagram of the surface of the ball sensor 24 illustrating the conductive strips forming the inductive element 1304. The conductive strips, referred to by reference numeral 1810, are spaced above the surface of the integrated circuit of the ball sensor by a predetermined distance, and separated therefrom by a layer of silicon dioxide. A passivation layer 1811 is then disposed over the upper surface of the conductive strips 1810. The conductive strips 1810 can be fabricated from polycrystalline silicon but, it would be preferable to form them from the upper metal layer to result in a higher conductivity strip. This will allow the strips 1810 to be narrower and separated from each other by a larger distance. This separation would reduce the amount of capacitance therebetween.

One end of the strip 1810 is connected to a diode structure 1813. The diode structure 1813 is formed of an N-well implant region 1814 into which a P-well implant region 1816 is disposed, and an N-well implant region 1818 disposed within the P-well implant region 1816. This forms a PN diode where one end of the conductive strips 1810, a conductive connection 1820, is connected to the P-well 1816 implant region, and a conductive layer 1822 is connected at one end to the N-well implant region 1818. This conductive layer or strip 1822 extends outward to other circuitry on the integrated circuit and can actually form the capacitor. Since it needs to go to a capacitor directly, a lower plate 1824 formed of a layer of polycrystalline silicon or metal in a double-metal process, could be provided separated therefrom by a layer of oxide.

Referring now to FIG. 19A, there are illustrated additional details of the monitor 24. The monitor 24 is hermetically protected by a thin exterior glass passivation layer 1952, which may be phosphosilicate glass (PSG). The interior of the ball monitor 24 comprises a semiconductor substrate 1954, which may be doped p-type or n-type in accordance with the particular requirements of the fabrication process. Optionally, the substrate 1954 may be connected to the metallic intraluminal device to serve as a ground potential for the monitor 24. A transducer 1928 (similar to transducer 115 of FIG. 7) has an outer surface 1956 that is exposed to the bloodstream flowing through the patient's artery (or to any other application which interfaces with fluids flowing in a body lumen). The transducer 1928 preferably is formed atop a thick dielectric layer 1958, which may be a field oxide layer grown on the substrate 1954.

A large number of transistors make up the circuitry of the voltage regulator 114, control logic 116 and RF transmitter 119, described above in connection with FIG. 7. Some of these transistors are depicted in FIG. 19A, and labeled with the letter "T." Although these transistors T are depicted schematically as field-effect transistors, the integrated circuitry of the monitor 24 could also use bipolar transistors. The individual transistors T are shown separated by portions of the field oxide 1958. Transistor gates G and circuit interconnections (not shown) are embedded in an inter-level dielectric layer 1960 and are made using conventional semiconductor fabrication techniques adapted to the spherical surface of the monitor 24.

The power coil 1929 (as described in connection with antenna/coil 111 of FIG. 7), is shown as having a plurality of separate windings 1962a, 1962b, 1962c and 1962d, which may be fabricated from a deposited layer of aluminum that is patterned and etched using conventional semiconductor fabrication techniques adapted to the spherical shape of the monitor 24. The windings are insulated from each other by portions of the inter-level dielectric layer 1960. The actual number of individual windings of the coil may be far greater than the four specific windings shown. The ends of the coil 1929 are connected by additional conductors (not shown) to other circuit elements of the monitor 24.

Referring now to FIG. 19B, there is illustrated an implementation of the transducer 28. By way of example, the transducer 28 may consist of a strain gauge fabricated atop the field oxide 1958, which strain gauge may be used to determine quantitative data related to pressure. A dome 1963 is supported at its periphery by the field oxide 1958 and defines a cavity 1965 between the dome and the field oxide 1958. The dome 1963 preferably comprises monocrystalline silicon and includes an elongated doped resistor 1967, which is indicated by the stippling at the outer surface of the silicon dome 1963. A dielectric layer 1969, such as silicon dioxide, overlies the dome 1963. Metal contacts 1971 and 1973 are formed atop the dielectric layer 1969 and extend therethrough to make contact with the opposite ends of the doped resistor 1967. The metal contacts 1971 and 1973 have extensions (not shown in the cross section) that interconnect the resistor with circuitry of the previously described control logic 116.

The strain gauge transducer 28 can be fabricated by forming a layer of selectively etchable material in the shape of the cavity 1965 atop the field oxide layer 1958. For example, a phosphorus doped oxide can be deposited on the surface of the device, and then patterned into the desired shape by photolithographic techniques adapted to the spherical shape of the device. Next, the silicon dome 1963 is formed, such as by the deposition of polycrystalline silicon followed by recrystallization. Alternatively, the monocrystalline silicon layer used to make the dome 1963 can be epitaxially grown, such as by seeding the growth from an exposed portion of the substrate 1954 adjacent to the field oxide 1958. Such techniques are known, as described in U.S. Pat. No. 4,754,314, entitled "Split-Level CMOS," issued Jun. 28, 1988. A patterning procedure is then used to define the ultimate shape of the periphery of the dome 1963. Then, peripheral ports (not shown) are etched at opposite sides of the dome 1963 down to the doped oxide layer. Next, the device is exposed to an acid that preferentially etches doped oxide at a much faster rate than undoped silicon dioxide. It is well known that hydrofluoric acid will etch phosphorus doped oxide at a much faster rate (e.g., 15 times faster) depending on the phosphorus doping level and oxide density. The acid flows into the peripheral ports and etches the doped oxide layer laterally beneath the silicon dome 1963 to create the cavity 1965. The acid is then flushed out to introduce air or other gas, such as nitrogen, into the cavity 1965. Then, the outer dielectric layer 1969 is formed followed by the contacts 1971 and 1973. The deposition of the silicon dioxide of the dielectric layer 1969 fills the peripheral ports and seals the cavity 1965.

In a variation of the foregoing technique, a thin silicon nitride layer (not shown) can be deposited on the field oxide layer 1958 to serve as an etch-stop layer, followed by the deposition and patterning of the selectively etchable oxide layer. Optionally, another thin silicon nitride layer can be deposited atop the patterned oxide layer prior to the formation of the silicon layer 1963. These additional steps can facilitate preferential lateral etching of the patterned oxide layer to create a cavity like the cavity 1965, since hydrofluoric acid etches oxide at a much faster rate (e.g., 50 times faster) than silicon nitride.

In operation, the strain gauge 28 senses pressure applied to the dome 1963 through the dielectric layers 1952 and 1969. As the pressure increases, the dome 1963 flexes downward very slightly, which also compresses the gas in the cavity 1965 to a slight degree. The resistance of the resistor 1967 varies in proportion to the variations in pressure of the fluid adjacent the outer surface 1956 of the dielectric layer 1952. The characteristics of semiconductor strain gauges are known in the art. A semiconductor strain gauge whose essential characteristics are similar to the strain gauge 1926 of FIG. 19B is described in U.S. Pat. No. 4,618,844, entitled "Semiconductor Pressure Transducer," issued Oct. 21, 1986, which is hereby incorporated by reference.

Other techniques may be used to integrate a pressure transducer onto the surface of a semiconductor ball. For example, variable capacitors, which are ideally suited for sensing pressure, can be fabricated using conventional semiconductor fabrication processes. A method of making a variable capacitor semiconductor transducer is described in U.S. Pat. No. 4,665,610, entitled "Method of Making a Semiconductor Transducer Having Multiple Level Diaphragm Structure," issued May 19, 1987, which is hereby incorporated by reference. Such a method or variations thereof can be adapted for fabrication on a spherical-shaped semiconductor substrate.

Referring now to FIG. 19C, there is illustrated a conventional strain gauge circuit according to the device structure of FIG. 19B. A conventional strain gauge architecture comprises a set of four resistances in the configuration of a Wheatstone bridge. Resistances R1, R2, R3 and R4 are connected end to end in a loop such that the output signals are pulled off opposing nodes 1980 (a node common to resistances R1 and R2) and node 1982 (a node common to resistances R3 and R4). In like fashion, the excitation voltage is applied at the remaining two opposing nodes 1984 (the point common between resistances R1 and R4) and node 1986 (the point common to resistances R2 and R3). The excitation voltage is supplied by a power source 1988 placed across the nodes 1984 and 1986. In the context of FIG. 19B, the consolidation of resistances R1, R2, R3 and R4 represent the elongated doped resistor 1967 illustrated in FIG. 19B. The elongated doped resistor 1967 may be tapped off at various points to obtain the illustrated Wheatstone bridge. The metal contacts 1971 and 1973 of FIG. 19B relate to the output terminals 1990 and 1992 which interface with the control logic 116. The power source 1988 may comprise a miniature self-contained battery system, as described hereinbelow, or may be provided externally from location 120 coupled into the monitor 24 and provided through voltage regulation 114 to the strain gauge transducer 28. When under strain, the elongated doped resistor 1967 flexes such that resistance values R1, R2, R3 and R4 are changed in proportion to the changing condition sensed. The output at nodes 1990 and 1992 is a voltage which varies in direct relationship to the parameter being measured by the strain gauge transducer 28.

Referring now to FIGURE 19D, there is illustrated a portion of a monitor 24', as modified from the embodiment of FIG. 19A using similar reference numerals which designate similar elements. The monitor 24' includes a substrate 1954' on which a thick field oxide 1958' has been grown. Overlying the thick field oxide 1958' is a pressure transducer 1928' whose outer surface has been modified in accordance with a disclosed embodiment. The portion of dielectric layer 1952' lying over the transducer 1928' has recesses 1964 formed in its outer surface. These recesses 1964 may also extend beyond the edges of the transducer 1928' at least so far as the monitor's surfaces may be exposed to the bloodstream.

The purpose of the recesses 1964 is to inhibit tissue adhesion to the surfaces of the monitor 24' that are exposed to the patient's blood. Tissue adhesion is known to occur on the surfaces of implants through the attachment of fibroblasts. This phenomenon is well known and is described in Von Recum et al., "Surface Roughness, Porosity, and Texture as Modifiers of Cellular Adhesion," *Tissue Engineering*, Vol. 2, No. 4, 1996 (available from the Dept. of Bioengineering, Clemson University, Clemson, S.C.). The recesses 1964 are presently preferred to be about one micron deep, three microns wide, and spaced three microns apart in a checkerboard topography. Such recesses can be fabricated by conventional selective etching techniques adapted to the spherical shape of the monitor 24.

From the foregoing disclosure, it can be appreciated that numerous limitations in the prior art can be solved through the use of ball sensors. The fluid column often used in pressure sensing can be eliminated by communicating with a large external sensor outside the body. Various catheter and guidewire exchanges would be eliminated thus making the procedure simpler, faster, and safer for the patient and physician. Internal site-specific sensors provide more clear and accurate signals with minimal artifacts for both position registration and functional measurements. Integration of ball sensors along the catheter, guidewire, or other insertable instrument with remote visualization capability allows for magnetic resonance imaging without harmful x-ray exposure for the patient and physician. In a similar manner, a combination of ultrasound emitters and sensors can illicit imaging for accurate positioning without x-ray exposure. Diagnostic and treatment capabilities can be combined on the same catheter, guidewire or insertable instrument. In some cases, external monitor connections are eliminated freeing the patient and caregivers from encumbrances making the entire system more user friendly and simple. Sensors located on a catheter may also allow for control and positioning of an atherectomy catheter relative to the atherosclerotic plaque.

The spherical geometry of the semiconductor ball devices disclosed herein offers a number of advantages compared to conventional semiconductor devices having a planar or two-dimensional geometry. By way of illustration, a few of these advantages include the following: a spherical device has a smooth, rounded shape which is easily implanted or injected into a biological medium and which passes easily through a biological medium if necessary in a particular application. Further, the large surface area of a spherical device relative to its overall dimensions provides for the maximum of surface area devoted to functional regions in contact with the biological medium such as transducers and other circuitry. Further, the spherical device permits disposition of transducers aligned on all three geometric axes for maximum transducer function on a single device.

Although the preferred embodiment has been described in detail, it should be understood that various changes, substitutions and alterations can be made therein without departing from the spirit and scope of the invention as defined by the appended claims.

What is claimed is:

1. A monitoring system, comprising:
   an instrument for insertion into a body, the instrument having a distal end for accessing a site within the body and a proximal end that remains outside of the body;
   one or more miniature semiconductor devices affixed at a point on the distal end of the instrument, the device including a transducer for converting information from one medium to another;

an external monitoring station in communication with the semiconductor device; and a communication device for effecting the transfer of information between the semiconductor device and the monitoring station;

wherein the transducer is capable of reporting information to a central processing unit in the monitoring station via radio frequency transmitted signals;

wherein the instrument is selected from the group consisting of a guidewire, a needle, and a catheter;

wherein the transducer is placed on the distal end of the instrument to deliver energy within the body;

and wherein the transducer is powered by radio frequency transmitted signals.

2. The monitoring system of claim 1, wherein the semiconductor device includes a spherical substrate on which the transducer resides together with integrated circuitry for processing signals in communication with the monitoring station.

3. The monitoring system of claim 1, wherein the transducer is capable of measuring pressure from within the body and communicating corresponding signals outside the body.

4. The monitoring system of claim 1, wherein the transducer is formed on a spherical surface portion of a substrate.

5. The monitoring system of claim 1, wherein the transducer is attached to and incorporated into a guidewire.

6. The monitoring system of claim 1, wherein the transducer is attached to and incorporated into an open hollow catheter.

7. The monitoring system of claim 1, wherein the transducer is attached to a needle, needle chamber, or intravenous tubing.

8. The monitoring system of claim 1, wherein the transducer is used on a guidewire in the vascular system.

9. The monitoring system of claim 1, wherein the transducer is used on a catheter in the urinary tract.

10. The monitoring system of claim 1, wherein the transducer is introduced into the biliary tract.

11. The monitoring system of claim 1, wherein the transducer is introduced into the gastrointestinal tract.

12. The monitoring system of claim 1, wherein the transducer is introduced into the uterus and cervix.

13. The monitoring system of claim 1, wherein the transducer is introduced into the tracheobronchial airways.

14. The monitoring system of claim 1, wherein the transducer is introduced into a body cavity or space in the abdomen, chest, cranium, or neck.

15. The monitoring system of claim 1, wherein the transducer measures results of various therapeutic maneuvers selected from the group consisting of angioplasty, stent placement, atherectomy, and balloon dilatation.

16. The monitoring system of claim 1, wherein the transducer measures various parameters in the cardiopulmonary circulations.

17. The monitoring system of claim 1, wherein the transducer delivers light energy, such as laser or infrared light.

18. The monitoring system of claim 1, wherein the transducer delivers sound energy, such as ultrasound.

19. The monitoring system of claim 1, wherein the transducer delivers electrical energy.

20. The monitoring system of claim 1, wherein a plurality of the semiconductors devices are interconnected to provide a plurality of functions in support of converting the information from one medium to another.

21. A method of monitoring bodily processes of a body, comprising the steps of:

providing an instrument for insertion into the body, the instrument having a distal end for accessing a site within the body and a proximal end that remains outside of the body;

providing one or more miniature semiconductor devices affixed at a point on the distal end of the instrument, the device including a transducer for converting information from one medium to another;

communicating with the semiconductor device using an external monitoring station; and transmitting information from the semiconductor device to the monitor station in response to the step of communicating;

wherein the transducer is capable of reporting information to a central processing unit in the monitoring station via radio frequency transmitted signals;

wherein the instrument is selected from the group consisting of a guidewire, a needle, and a catheter;

wherein the transducer is placed on the distal end of the instrument to deliver energy within the body;

and wherein the transducer is powered by radio frequency transmitted signals.

22. The method of claim 21, wherein the semiconductor device includes a spherical substrate on which the transducer resides together with an integrated circuitry for processing signals in communication with the monitoring station.

23. The method of claim 21, wherein the transducer is capable of measuring pressure from within the body and communicating corresponding signals outside of the body.

24. The method of claim 21, wherein the transducer is formed on a spherical surface portion of a substrate.

25. The method of claim 21, wherein the transducer is attached to and incorporated into a guidewire.

26. The method of claim 21, wherein the transducer is attached to and incorporated into an open hollow catheter.

27. The method of claim 21, wherein the transducer is attached to a needle, needle chamber, or intravenous tubing.

28. The method of claim 21, wherein the transducer is used on a guidewire in the vascular system.

29. The method of claim 21, wherein the transducer is used on a catheter in the urinary tract.

30. The method of claim 21, wherein the transducer is introduced into the biliary tract.

31. The method of claim 21, wherein the transducer is introduced into the gastrointestinal tract.

32. The method of claim 21, wherein the transducer is introduced into the uterus and cervix.

33. The method of claim 21, wherein the transducer is introduced into the tracheobronchial airways.

34. The method of claim 21, wherein the transducer is introduced into a body cavity or space in the abdomen, chest, cranium, or neck.

35. The method of claim 21, wherein the transducer measures results of various therapeutic maneuvers selected from the group consisting of angioplasty, stent placement, atherectomy, and balloon dilatation.

36. The method of claim 21, wherein the transducer measures various parameters in the cardiopulmonary circulations.

37. The method of claim 21, wherein the transducer delivers light energy, such as laser or infrared light.

38. The method of claim 21, wherein the transducer delivers sound energy, such as ultrasound.

39. The method of claim 21, wherein the transducer delivers electrical energy.

40. The method of claim 21, wherein a plurality of the semiconductor devices are interconnected to provide a plurality of functions in support of converting the information from one medium to another.

* * * * *